(12) United States Patent
Kitamura et al.

(10) Patent No.: US 10,748,279 B2
(45) Date of Patent: Aug. 18, 2020

(54) IMAGE PROCESSING APPARATUS, IMAGE PROCESSING METHOD, AND COMPUTER READABLE RECORDING MEDIUM

(71) Applicant: OLYMPUS CORPORATION, Tokyo (JP)

(72) Inventors: Makoto Kitamura, Hachioji (JP); Mitsutaka Kimura, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 160 days.

(21) Appl. No.: 16/013,181

(22) Filed: Jun. 20, 2018

(65) Prior Publication Data
US 2018/0365830 A1 Dec. 20, 2018

Related U.S. Application Data

(63) Continuation of application No. PCT/JP2015/086086, filed on Dec. 24, 2015.

(51) Int. Cl.
*G06T 7/00* (2017.01)
*A61B 1/00* (2006.01)
(Continued)

(52) U.S. Cl.
CPC .......... *G06T 7/0012* (2013.01); *A61B 1/005* (2013.01); *A61B 1/00009* (2013.01); *A61B 1/041* (2013.01); *G06K 9/00362* (2013.01); *G06T 7/11* (2017.01); *G06T 7/90* (2017.01); *H04N 5/2351* (2013.01); *G06K 2209/051* (2013.01); *G06T 2207/10024* (2013.01); *G06T 2207/10068* (2013.01); *G06T 2207/30028* (2013.01);
(Continued)

(58) Field of Classification Search
None
See application file for complete search history.

(56) References Cited

U.S. PATENT DOCUMENTS 8,903,167 B2    12/2014  Kohli et al.
2012/0288186 A1*  11/2012  Kohli .............. G06K 9/6255
                                                          382/159
2016/0379363 A1   12/2016  Kitamura et al.

FOREIGN PATENT DOCUMENTS

JP    H07-021367 A      1/1995
JP    3347817 B2 *     11/2002
(Continued)

OTHER PUBLICATIONS

International Search Report dated Mar. 8, 2016 issued in International Application No. PCT/JP2015/086086.
(Continued)

*Primary Examiner* — Delomia L Gilliard
(74) *Attorney, Agent, or Firm* — Scully, Scott, Murphy & Presser, P.C.

(57) ABSTRACT

An image processing apparatus includes: an image acquiring unit configured to acquire a lumen image of a living body; an image generating unit configured to generate a plurality of new images by changing at least one of a hue and a brightness of the lumen image to predetermined values based on range information in which a range of at least one of a hue and a brightness is set in advance according to biometric information included in the lumen image; and a learning unit configured to learn identification criteria to perform identification of a subject based on the images.

18 Claims, 9 Drawing Sheets

(51) Int. Cl.
  *G06T 7/11* (2017.01)
  *G06T 7/90* (2017.01)
  *A61B 1/005* (2006.01)
  *A61B 1/04* (2006.01)
  *G06K 9/00* (2006.01)
  *H04N 5/235* (2006.01)
  *H04N 9/64* (2006.01)
  *H04N 5/225* (2006.01)

(52) U.S. Cl.
  CPC ...... *G06T 2207/30092* (2013.01); *H04N 9/64* (2013.01); *H04N 2005/2255* (2013.01)

(56) References Cited

FOREIGN PATENT DOCUMENTS

| | | |
|---|---|---|
| JP | 3347817 B2 | 11/2002 |
| JP | 2007-236957 A | 9/2007 |
| JP | 2007236957 A * | 9/2007 |
| JP | 2013-240701 A | 12/2013 |
| JP | 2013240701 A * | 12/2013 |
| JP | 2014-023566 A | 2/2014 |
| JP | 2014023566 A * | 2/2014 |
| JP | 2015-173827 A | 10/2015 |
| JP | 2015173827 A * | 10/2015 |

OTHER PUBLICATIONS

Japanese Office Action dated Sep. 24, 2019 in Japanese Patent Application No. 2017-557592.
Chinese Office Action dated Nov. 18, 2019 in Chinese Patent Application No. 201580085814.2.

* cited by examiner

IMAGE PROCESSING APPARATUS, IMAGE PROCESSING METHOD, AND COMPUTER READABLE RECORDING MEDIUM

CROSS-REFERENCE TO RELATED APPLICATION

This application is a continuation of International Application No. PCT/JP2015/086086, filed on Dec. 24, 2015, the entire contents of which are incorporated herein by reference.

BACKGROUND

The present disclosure relates to an image processing apparatus, an image processing method, a computer-readable recording medium for performing image processing on an image that is acquired by imaging a lumen of a living body.

The technique of detecting a specific region, such as an abnormal region, based on identification criteria for a lumen image that is acquired by imaging a lumen (inside of a digestive tract) of a living body by using a medical observation device, such as an endoscope has been known. The identification criteria used therefor are usually created based on various images of mucous membranes or abnormal regions that have been extracted from lumen images as learning samples.

As the technique related to identification of images, for example, U.S. Pat. No. 8,903,167 discloses a technique in which a new image is generated by performing geometric processing, such as to change a position, a direction, and an appearance of an arbitrary region of interest, and to enlarge, reduce, or rotate a region of interest, on an image acquired as a learning sample, and identification criteria are generated by calculating feature amounts from the new image and the original image.

SUMMARY

An image processing apparatus according to one aspect of the present disclosure includes: an image acquiring unit configured to acquire a lumen image of a living body; an image generating unit configured to generate a plurality of new images by changing at least one of a hue and a brightness of the lumen image to predetermined values based on range information in which a range of at least one of a hue and a brightness is set in advance according to biometric information included in the lumen image; and a learning unit configured to learn identification criteria to perform identification of a subject based on the images.

The above and other features, advantages and technical and industrial significance of this disclosure will be better understood by reading the following detailed description of presently preferred embodiments of the disclosure, when considered in connection with the accompanying drawings.

DETAILED DESCRIPTION

First Embodiment

Configuration of Image Processing Apparatus

Figure 1:
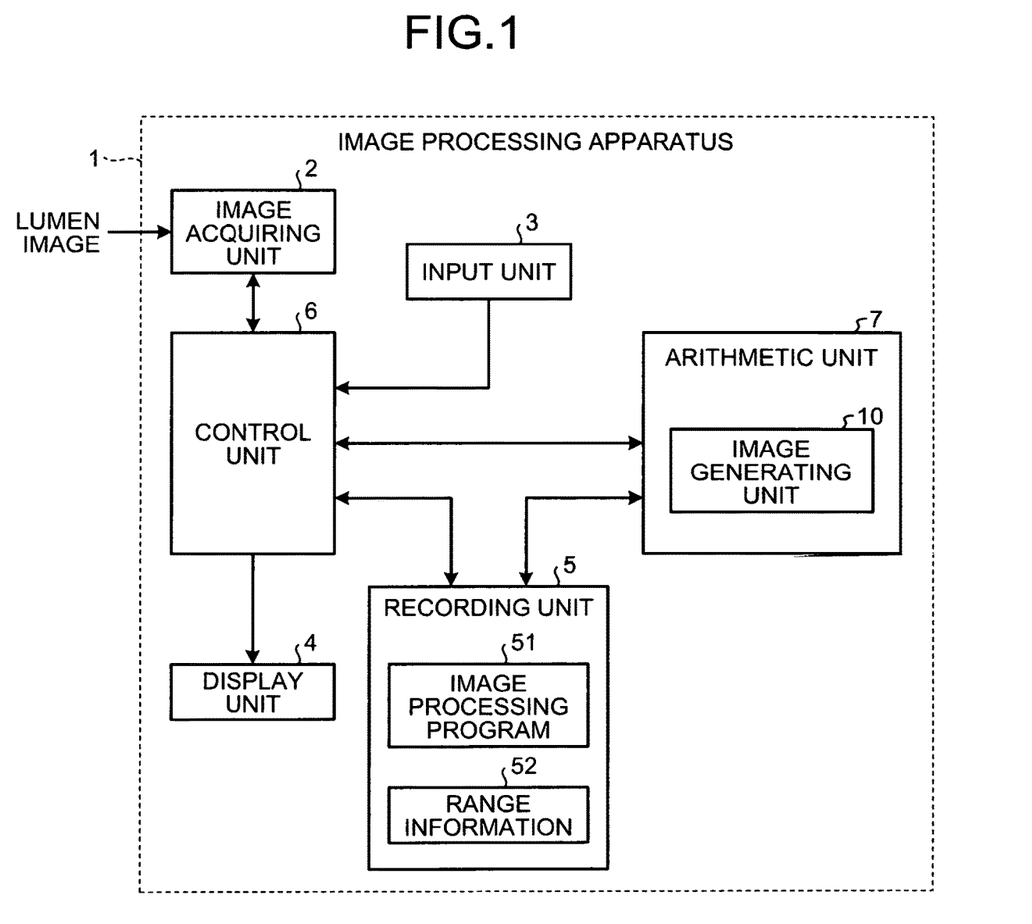
FIG. 1 is a block diagram illustrating a configuration of an image processing apparatus according to a first embodiment.

FIG. 1 is a block diagram illustrating a configuration of an image processing apparatus according to a first embodiment. An image processing apparatus 1 according to the first embodiment is an apparatus that performs image processing to generate a new image (a virtual image or a learning sample) in which a color or a brightness of a lumen image is changed based on biometric information of the lumen image that is acquired by imaging a lumen of a living body by using an endoscope (flexible endoscope, inflexible endoscope, and the like) or a capsule endoscope (hereinafter, these are collectively referred to as "endoscope" simply) as an example. The lumen image is generally a color image having respective pixel levels (pixel values) corresponding to wavelength components of R (red), G (green), B (blue) at each pixel position.

The image processing apparatus 1 illustrated in FIG. 1 includes an image acquiring unit 2 that outputs image data corresponding to a lumen image that is imaged by an endoscope from the endoscope or an external unit, an input unit 3 that accepts an input signal that is input by an external operation, a display unit that displays the lumen image or various displays, a recording unit 5 that records image data that is acquired by the image acquiring unit 2 or various kinds of programs, a control unit 6 that controls overall operations of the image processing apparatus 1, and an arithmetic unit 7 that performs predetermined image processing on image data.

The image acquiring unit 2 is configured appropriately according to a mode of a system including an endoscope. For example, when a portable recording medium is used to communicate image data with an endoscope, the image acquiring unit 2 is configured as a reader device that detachably mounts the recording medium and that reads recorded image data. Moreover, when imager data acquired by an endoscope is recorded by a server, the image acquiring unit 2 can be configured with a communication device, or the like that can communicate with this server interactively, and acquires the image data by performing data communication with the server. Furthermore, the image acquiring unit 2 can be configured with an interface device, or the like to which image data is input through a cable from an endoscope.

The input unit 3 is implemented by an input device such as a keyboard, a mouse, a touch panel, and various kinds of switches, and outputs an input signal that is accepted in response to an external operation, to the control unit 6.

A display unit 4 is implemented by a display device such as a liquid crystal or an organic electroluminescence (EL) display panel, and displays various kinds of screens including a lumen image under control of the control unit 6.

The recording unit 5 is implemented by various kinds of integrated circuit (IC) memory devices such as a flash memory, a read-only memory (ROM) and a random access memory (RAM), a hard disk that is integrated therein or connected by a data communication terminal, or the like. The recording unit 5 records, in addition to image data that is acquired by the image acquiring unit 2, a program to cause the image processing apparatus 1 to perform various functions, data that is used during execution of the program, and the like. For example, the recording unit 5 records, for example, an image processing program 51 to generate a new image (learning sample) in which a color or a brightness of a lumen image is changed, range information about a range of hue and/or brightness set based on biometric information of a lumen image for the arithmetic unit 7 described later to generate a new image in which a hue and/or a brightness of the lumen image are/is changed, and various kinds of information that are used during execution of this program.

The control unit 6 is implemented by using a central processing unit (CPU) or the like, and gives instructions to respective parts constituting the image processing apparatus 1, and performs data transfer and the like according to image data input from the image acquiring unit 2 or an input signal input from the input unit 3 by reading various kinds of programs recorded in the recording unit 5, and performs overall control of entire operation of the image processing apparatus.

The arithmetic unit 7 is implemented by a CPU or the like, and performs image processing to generate a new image in which a color or a brightness of a lumen image is changed based on biometric information of the lumen image by reading the image processing program 51 recorded in the recording unit 5.

Configuration of Arithmetic Unit.

Next, a detailed configuration of the arithmetic unit 7 is explained. The arithmetic unit 7 includes an image generating unit 10. The image generating unit 10 generates a new image in which a color or a brightness of a lumen image is changed based on biometric information of the lumen image.

Processing of Image Processing Unit

Figure 2:
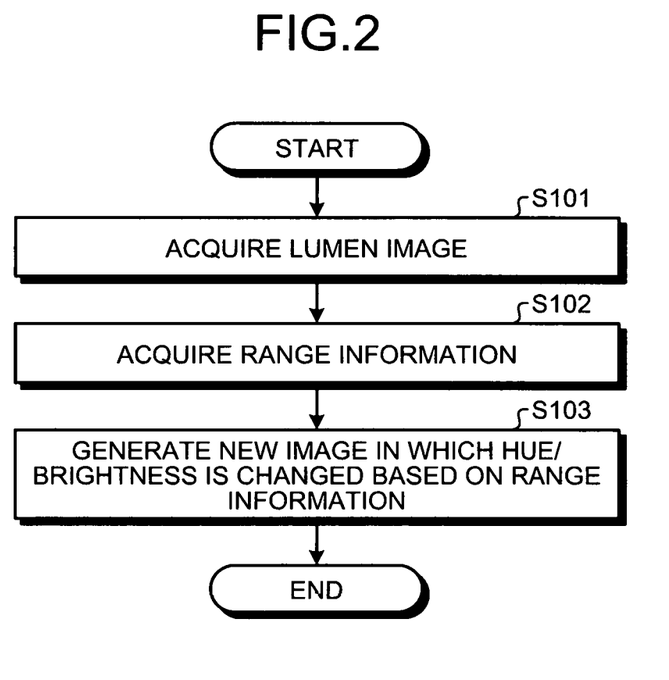
FIG. 2 is a general flowchart of processing that is performed by the image processing apparatus according to the first embodiment.

Next, an image processing method that is performed by the image processing apparatus 1 is explained FIG. 2 is a general flowchart of processing that is performed by the image processing apparatus 1. As illustrated in FIG. 2, first, the image generating unit 10 acquires a lumen image that corresponds to image data that has been externally acquired by an endoscope or the like through the image acquiring unit 2 (step S101).

Subsequently, the image generating unit 10 acquires range information in which a range of both of hue and brightness are or one of hue and brightness is set based on biometric information of the lumen image (step S102).

Thereafter, the image generating unit 10 generates multiple new images by varying the color or the brightness of the lumen image at predetermined intervals based on the lumen image acquired at step S101 and the range information acquired at step S102, and causes the recording unit 5 to record or the display unit 4 to display the generated images (step S103). The image generating unit 10 can output the generated new images to an external device that has a learning function or an identification function. After step S103, the image processing apparatus 1 ends this processing.

According to the first embodiment explained above, a learning sample having colors that can appear in a lumen image can be generated.

Second Embodiment

Next, a second embodiment is explained. An image processing apparatus according to the second embodiment has a different configuration in the arithmetic unit 7 from the image processing apparatus 1 according to the first embodiment described above. In the following a configuration of an arithmetic unit according to the second embodiment is explained. Common reference symbols are assigned to common parts with the image processing apparatus 1 according to the first embodiment, and explanation thereof is omitted.

Configuration of Arithmetic Unit

Figure 3:
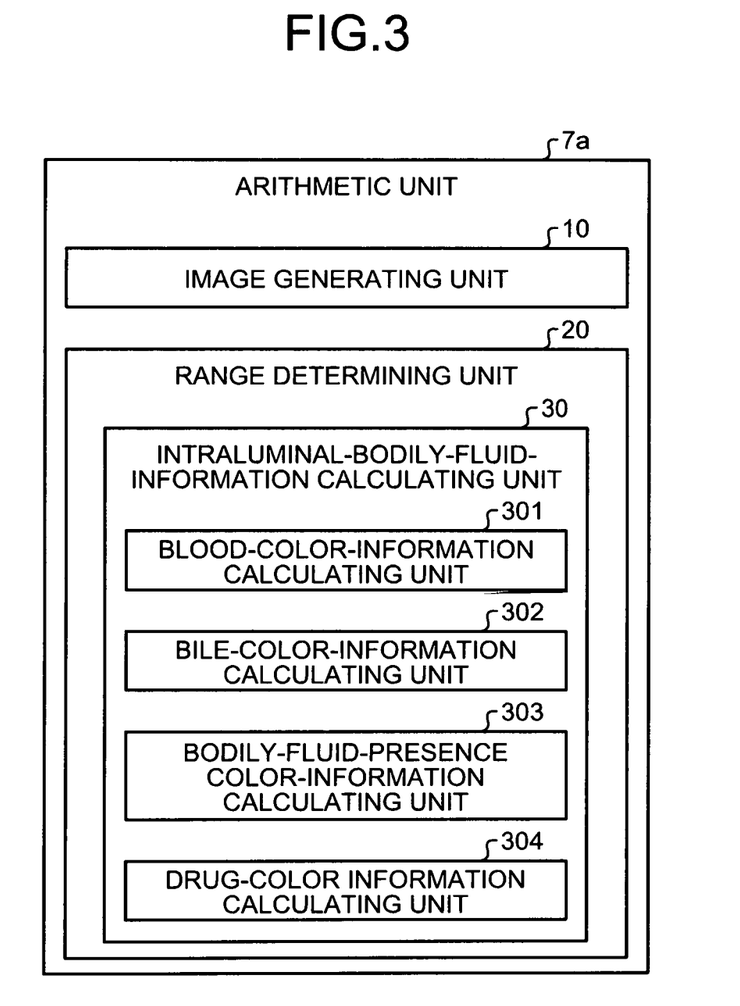
FIG. 3 is a block diagram illustrating a configuration of an arithmetic unit according to a second embodiment.

FIG. 3 is a block diagram illustrating a configuration of the arithmetic unit according to the second embodiment. An arithmetic unit 7a includes the image generating unit 10 and a range determining unit 20.

The range determining unit 20 generates range information to determine a range of color or brightness based on biometric information. The range determining unit 20 includes an intraluminal-bodily-fluid-information calculating unit 30.

The intraluminal-bodily-fluid-information calculating unit 30 includes a blood-color-information calculating unit 301, a bile-color-information calculating unit 302, a bodily-fluid-presence color-information calculating unit 303, and a drug-color-information calculating unit 304.

The blood-color-information calculating unit 301 determines information relating to a color range of blood. Specifically, the blood-color-information calculating unit 301 determines a color range of red.

The bile-color-information calculating unit 302 determines information relating to a color range of bile. Specifically, the bile-color-information calculating unit 302 determines a color range of yellow.

The bodily-fluid-presence color-information calculating unit 303 determines information relating to a color range according to presence or absence of a bodily fluid. Specifically, a color range of red and a brightness are determined based on the information relating to a color range according to presence or absence of a bodily fluid.

The drug-color-information calculating unit 304 determines information relating to a color range of drug. Specifically, the drug-color-information calculating unit 304 determines a color range of white and a brightness based on laxative type information.

Processing of Image Processing Apparatus

Figure 4:
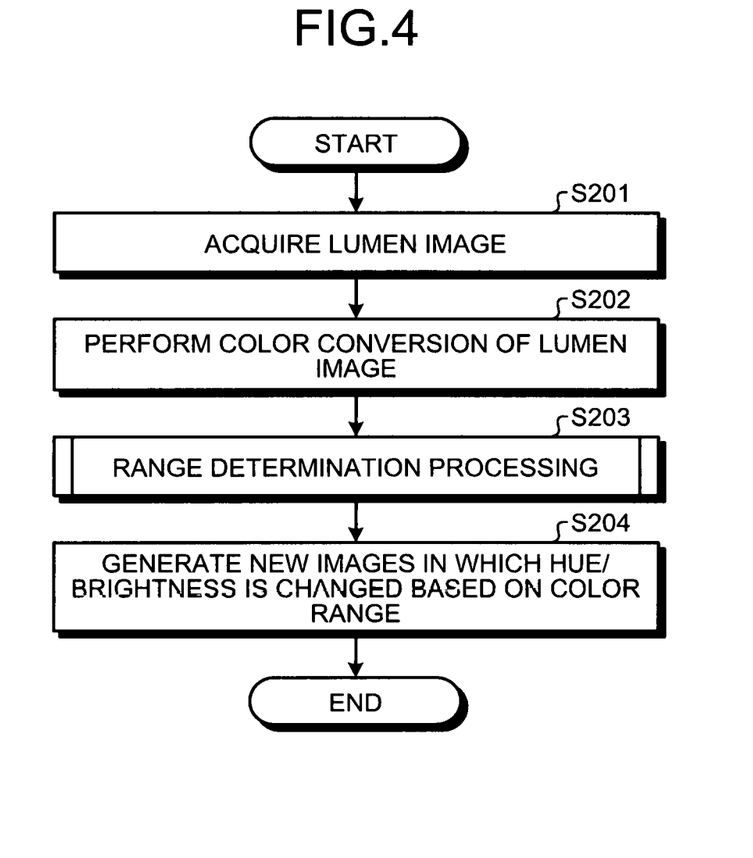
FIG. 4 is a general flowchart of processing that is performed by an image processing apparatus according to the second embodiment.

Next, an image processing method that is performed by the image processing apparatus 1 according to the second embodiment is explained. FIG. 4 is a general flowchart of processing that is performed by the image processing apparatus 1.

As illustrated in FIG. 4, first, the image generating unit 10 acquires a lumen image that corresponds to image data that has been externally acquired by an endoscope or the like through the image acquiring unit 2, and records the acquired lumen image in the recording unit 5 (step S201).

Subsequently, the image generating unit 10 subjects the lumen image to color conversion (step S202). Specifically, the image generating unit 10 color converts the lumen image from an RGB image to an HSV image. The color conversion method is not limited to the HSV, but other color conversion enabling to express hue and brightness, such as Lab, HLS, and YUV, can be applied.

Thereafter, the range determining unit 20 performs range determination processing of determining range information for the image generating unit 10 to generate a new image in which a hue and a brightness are changed based on the lumen image (step S203).

Range Determination Processing

Figure 5:
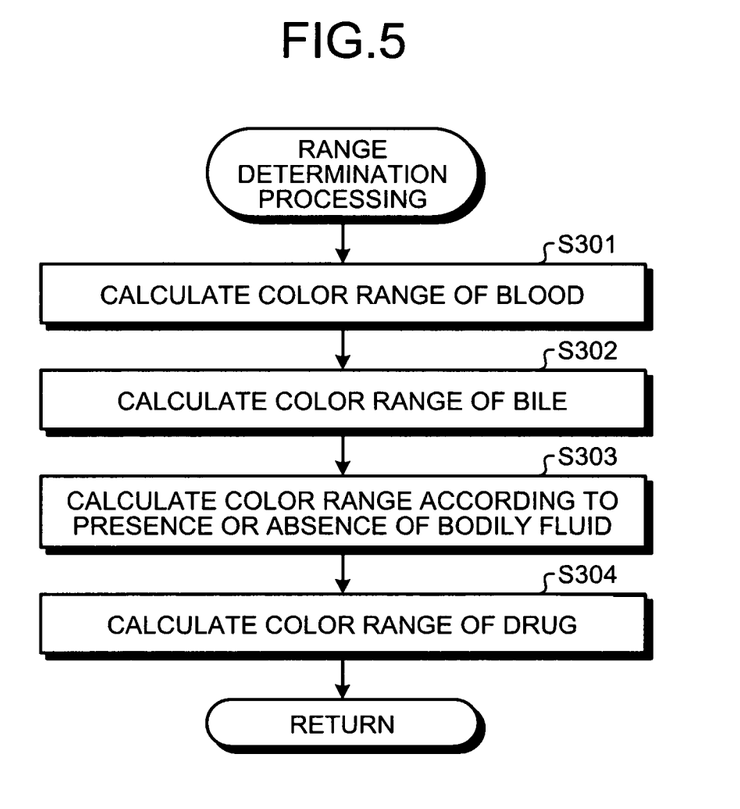
FIG. 5 is a general flowchart of range determination processing in FIG. 4.

FIG. 5 is a flowchart illustrating details of the range determination processing at step S203 in FIG. 4.

As illustrated in FIG. 5, the blood-color-information calculating unit 301 calculates information relating to a color range of blood (step S301). Specifically, because an absorption wavelength of hemoglobin, which is a component of blood, is in a band of mid-wavelength to short wavelength forming a G value or a B value, when blood is mixed in bodily fluids in a lumen in a body, the color is to be a color in the red range in which the G value and the B value are low relative to an R value. Therefore, in the second embodiment, images when blood is mixed in bodily fluids in a lumen of a living body are collected in advance, and an H (hue) range when blood is mixed is estimated. That is, the blood-color-information calculating unit 301 determines a color range of blood based on the preestimated H range when blood is mixed.

Subsequently, the bile-color-information calculating unit 302 calculates information relating to a color range of bile (step S302). Specifically, because an absorption wavelength of bilirubin, which is a component of bile, is in a band of short wavelength forming a B value, when bile is mixed in bodily fluids in a lumen in a living body, the color is to be a color in the yellow range in which the R value and the G value are high relative to the B value. Therefore, in the second embodiment, images when bile is mixed in bodily fluids in a lumen of a living body are collected in advance, and an H (hue) range when bile is mixed is estimated. That is, the bile-color-information calculating unit 302 determines a color range of bile based on the preestimated H range when bile is mixed.

Thereafter, the bodily-fluid-presence color-information calculating unit 303 calculates information relating to a color range according to presence or absence of a bodily fluid (step S303). With capsule endoscopes, images are captured in a state in which a bodily fluid is present in a lumen of a living body in many cases, but with flexible endoscopes, images are captured in a state in which a bodily fluid is not present in a lumen of a living body. Images captured without a bodily fluid tend to be dark-red images (red and dark images) compared to images captured in a state in which a bodily fluid is present. Therefore, in the second embodiment, images that are captured in a state in which a bodily fluid is absent and images that are captured through a bodily fluid are respectively collected in advance, and an H (hue) range in the state without a bodily fluid, and an H (hue) range and a V range (value) in the state with a bodily fluid are respectively estimated. That is, the bodily-fluid-presence color-information calculating unit 303 determines a color range in a state without a bodily fluid based on the preestimated H range and V range in the state without a bodily fluid, and determines a color range in the state with a bodily fluid based on the preestimated H range and V range in the state with a bodily fluid.

Subsequently, the drug-color-information calculating unit 304 calculates information relating to a color range of drug (step S304). In the second embodiment, images when a drug (for example, a laxative, a peristalsis stimulator, a booster, and the like) taken by an examination subject is mixed are collected in advance, and an H (hue) range when a drug is mixed is estimated. That is, the drug-color-information calculating unit 304 determines a color range of drug based on the preestimated H (hue) range in a state in which a drug is mixed. After step S304, the image processing apparatus 1 returns to the main routine in FIG. 4.

Subsequently, the image generating unit 10 generates a new image in which a hue and a brightness are changed based on the lumen image that is acquired at step S201 and the color range information that is determined by the range determining unit 20 at step S203 (step S204). For example, the image generating unit 10 generates plural images in which both of a hue and a brightness are or one of a hue and a brightness is varied every predetermined values for an entire image, for each predetermined range, and for each predetermined pixels. Thus, new images in which the colors or brightness is changed considering colors that can appear in a lumen image can be generated. After step S204, the image processing apparatus 1 ends this processing.

According to the second embodiment described above, learning samples with colors that can appear in a lumen image can be generated and, therefore, appropriate learning samples can be generated.

Third Embodiment

Next, a third embodiment is explained. An image processing apparatus according to the third embodiment differs in the configuration of the arithmetic unit 7a according to the second embodiment described above. In the following, a configuration of an arithmetic unit according to the third embodiment is explained. Common reference symbols are assigned to common parts with the image processing apparatus 1 according to the second embodiment described above, and explanation thereof is omitted.

Configuration of Arithmetic Unit

Figure 6:
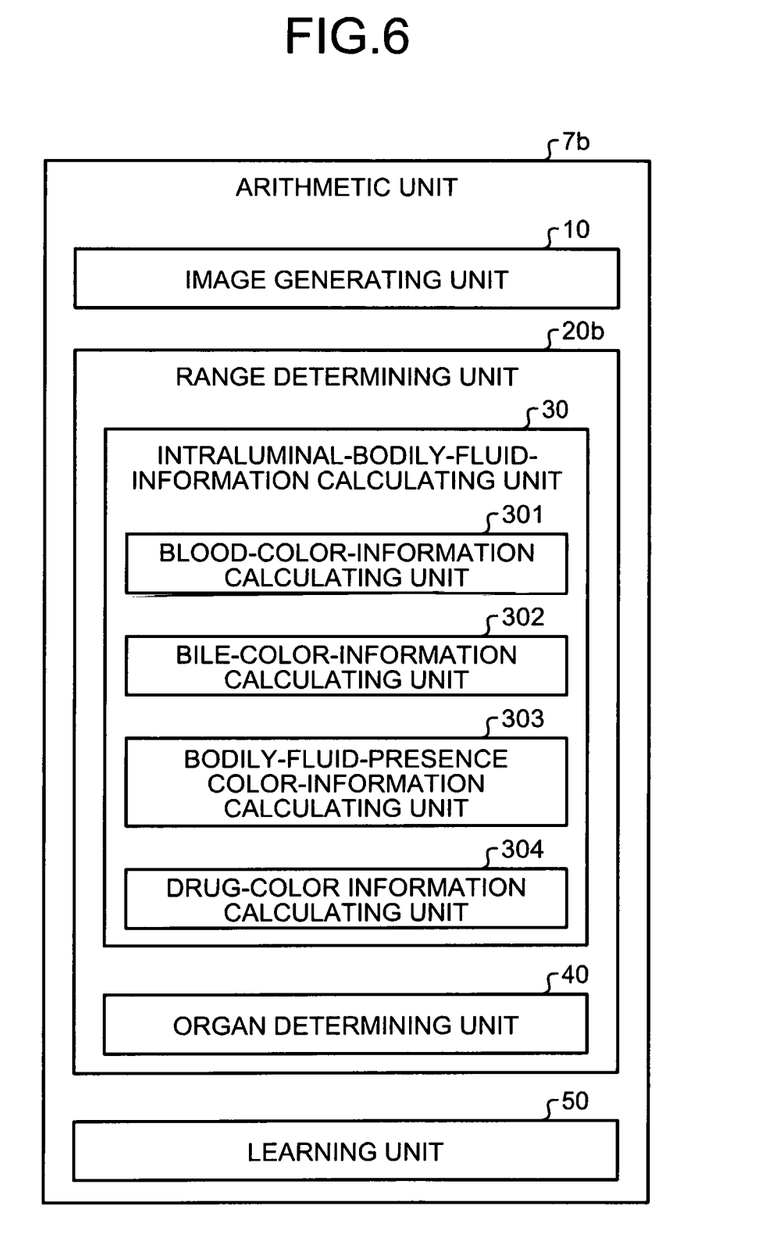
FIG. 6 is a block diagram illustrating a configuration of an arithmetic unit according to a third embodiment.

FIG. 6 is a block diagram illustrating a configuration of the arithmetic unit according to the third embodiment. An arithmetic unit 7b illustrated in FIG. 6 includes the image generating unit 10, a range determining unit 20b, and a learning unit 50.

The range determining unit 20b includes, in addition to the intraluminal-bodily-fluid-information calculating unit 30 according to the second embodiment described above, an organ determining unit 40 that determines an organ type of a lumen image.

The learning unit 50 learns identification criteria for performing identification of a subject based on new images generated by the image generating unit 10.

Processing of Image Processing Apparatus

Figure 7:
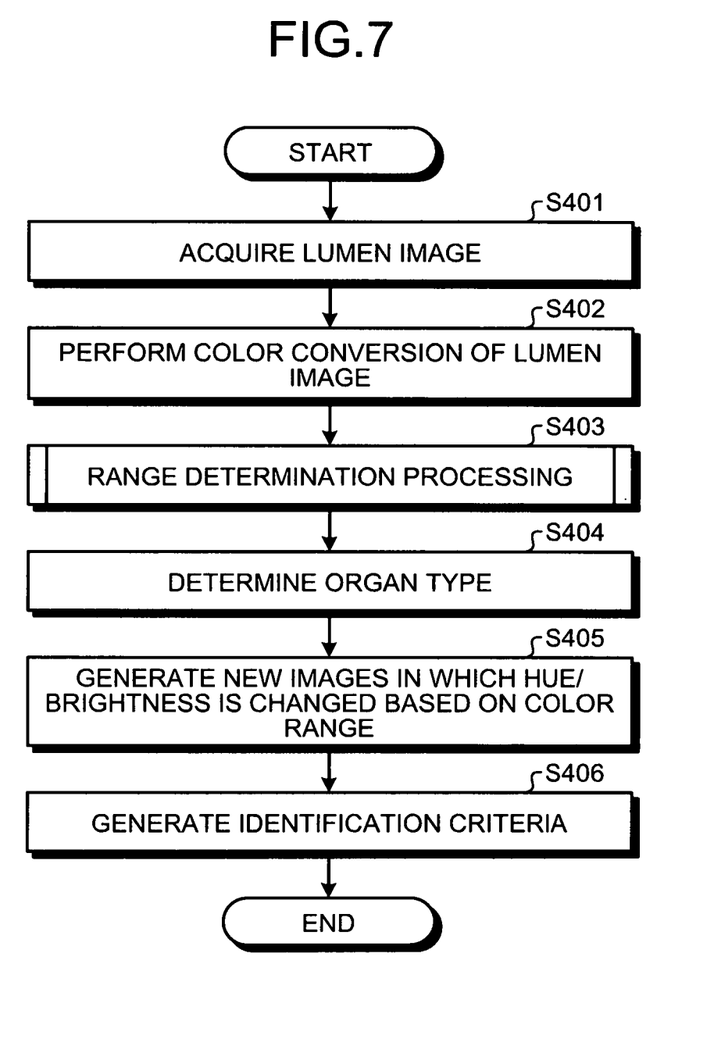
FIG. 7 is a general flowchart of processing that is performed by an image processing apparatus according to the third embodiment.

Next, an image processing method that is performed by the image processing apparatus 1 according to the third embodiment is explained. FIG. 7 is a general flowchart of processing performed by the image processing apparatus 1. Step S401 to step S403 correspond to step S201 to step S203 in FIG. 4 described above, respectively.

At step S404, the organ determining unit 40 determines an organ type of a lumen image. As a determination method of an organ type, for example, a method of determining an organ type based on average values of the R value, the G value, and the B value of a lumen image disclosed in Japanese Laid-Open Patent Publication No. 2006-288612 is used. Specifically, the organ determining unit 40 first determines numeric values of averages of the R value, the G value, and the B value in respective images of a stomach, a small intestine, and a large intestine in advance. Thereafter, the organ determining unit 40 determines the lumen image of a determination subject as that of a stomach when the respective average values of the R value, the G value, and the B value in the lumen image are within the range of the numeric values of stomach, determines the lumen image of a determination subject as that of a small intestine when within the range of the numeric values of small intestine, and determines the lumen image of a determination subject as that of a large intestine when within the range of the numeric values of large intestine.

Subsequently, the image generating unit 10 generates a new image in which one of a hue and brightness is or both of a hue and brightness are changed based on the color range determined by the range determining unit 20b (step S405). Specifically, the image generating unit 10 generates plural images in which both of a hue and a brightness are or one of a hue and a brightness is varied every predetermined values for an entire image, for each predetermined range, and for each predetermined pixels. In this case, when the organ determining unit 40 has determined that the organ type of the lumen image is stomach at step S404 described above, the image generating unit 10 excludes the color range of a bodily fluid including bile from the color ranges to be used when generating new images because bile is not present in the lumen image.

Thereafter, the learning unit 50 calculates feature amounts based on the new images generated by the image generating unit 10 and the original lumen image that is acquired through the image acquiring unit 2, and generates identification criteria by the publicly-known SVM (refer to pp. 95 to 102 of "Computer Vision and Image Media 6", Advanced Communication Media Co., Ltd.), and the like (step S406). After step S406, the image processing apparatus 1 ends this processing.

According to the third embodiment explained above, learning samples with colors that can appear in a lumen image can be generated and, therefore, appropriate learning results can be acquired.

Fourth Embodiment

Next, a fourth embodiment is explained. An image processing apparatus according to the fourth embodiment differs in a configuration of the arithmetic unit 7b according to the third embodiment described above. In the following, a configuration of an arithmetic unit according to the fourth embodiment is explained. Common reference symbols are assigned to common parts with the image processing apparatus 1 according to the third embodiment, and explanation thereof is omitted.

Configuration of Arithmetic Unit

Figure 8:
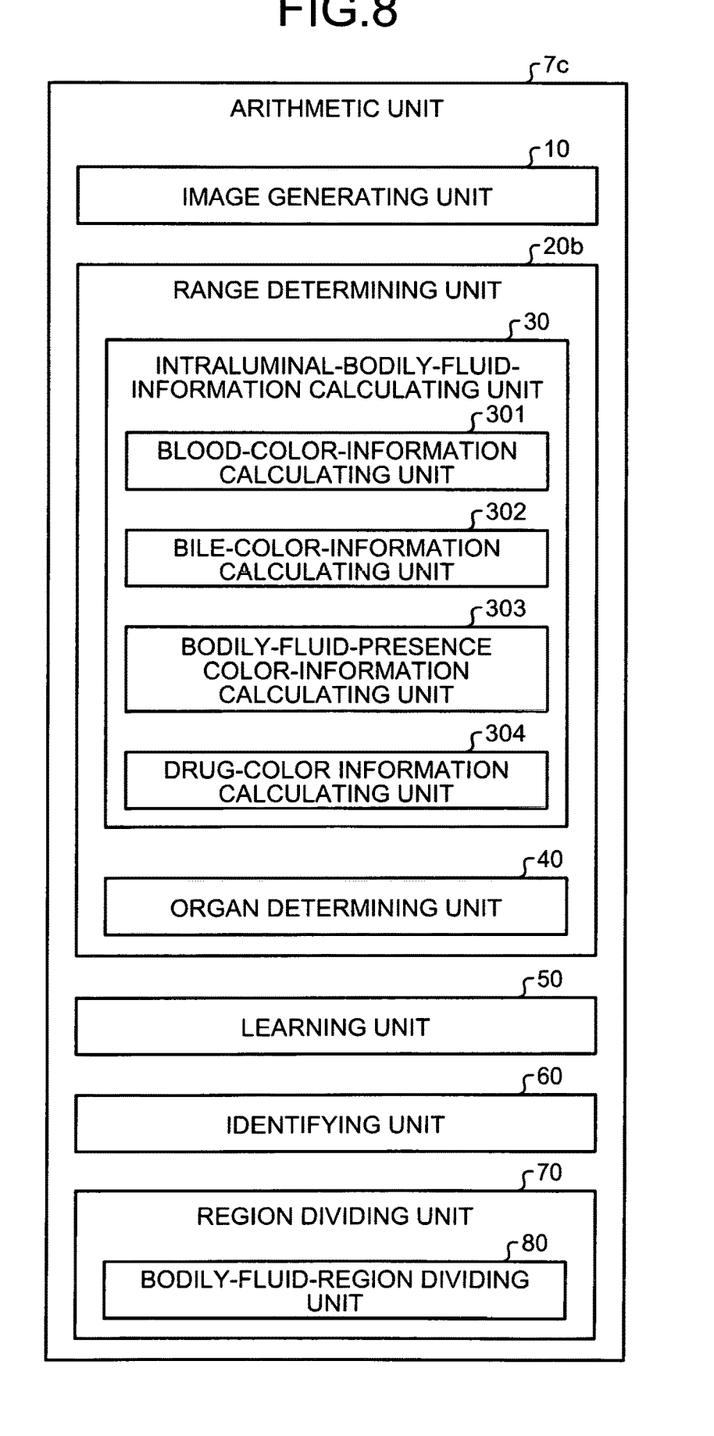
FIG. 8 is a block diagram illustrating a configuration of an arithmetic unit according to a fourth embodiment.

FIG. 8 is a block diagram illustrating a configuration of the arithmetic unit according to the fourth embodiment. An arithmetic unit 7c illustrated in FIG. 8 includes, in addition to the configuration of the arithmetic unit 7b according to the third embodiment described above, an identifying unit 60 that performs subject identification based on the identification criteria learned by the learning unit 50, and a region dividing unit 70 that performs region division. The region dividing unit 70 includes a bodily-fluid-region dividing unit 80 that divides into regions based on information of bodily fluid.

Processing of Image Processing Apparatus

Figure 9:
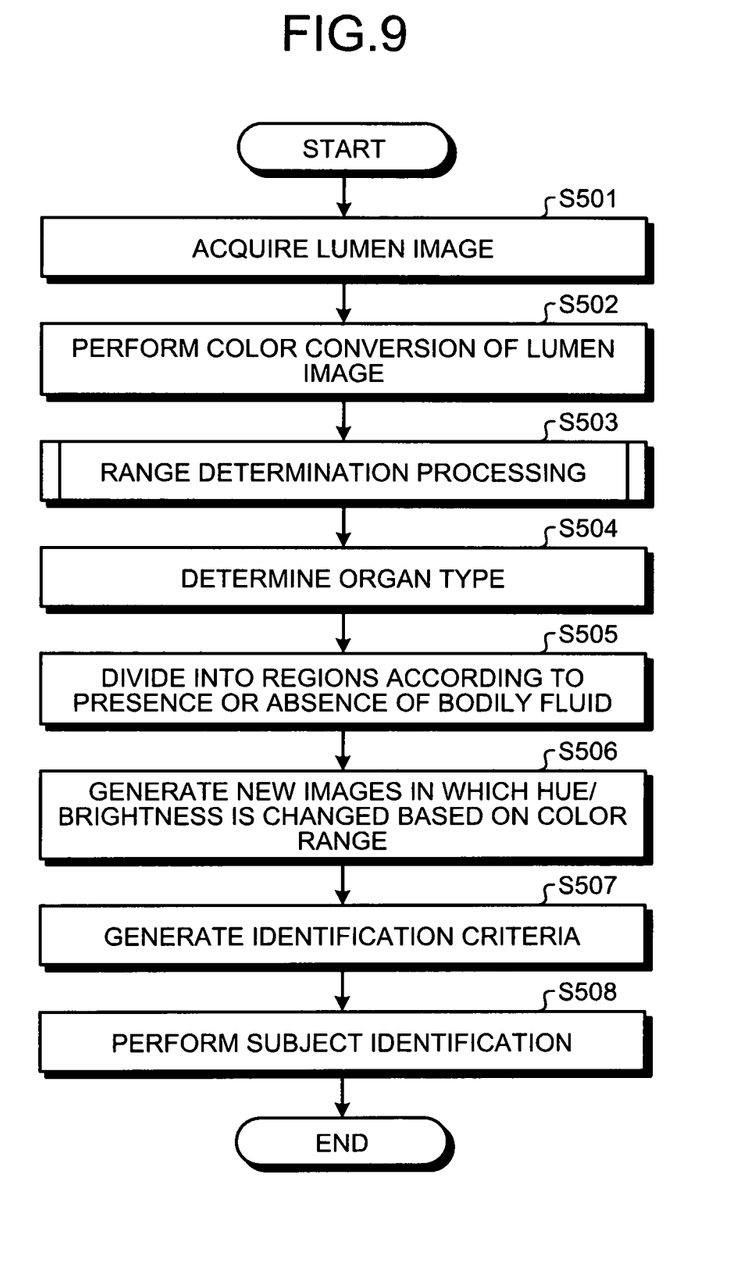
FIG. 9 is a general flowchart of processing that is performed by an image processing apparatus according to the fourth embodiment.

Next, processing performed by the image processing apparatus 1 according to the fourth embodiment is explained. FIG. 9 is a flowchart of processing that is performed by the image processing apparatus 1 according to the fourth embodiment. In FIG. 9, step S501 to step S504 correspond to S401 to step S404 in FIG. 7 described above, respectively.

At step S505, the region dividing unit 70 performs region division according to presence or absence of a bodily fluid. Specifically, first, the region dividing unit 70 determines the R value, the G value, and the B value of a lumen image with a bodily fluid, and determines the R value, the G value, and the B value of a lumen image without a bodily fluid in advance. Thereafter, the region dividing unit 70 determines that a bodily fluid is present when the R value, the G value, and the B value in a lumen image are within the range of numeric value of a case with a bodily fluid, and determines that a bodily fluid is absent when within the range of numeric value of a case without a bodily fluid. Furthermore, the region dividing unit 70 divides into regions by performing publicly-known labeling processing based on the information indicating presence or absence of a bodily fluid.

Subsequently, the image generating unit 10 generates a new image in which both of a hue and a brightness are or one of a hue and a brightness is changed based on the range information at step S503, the organ type at step S504, and the region division result at step S505 described above (step S506). Specifically, the image generating unit 10 generates plural new images in which a hue is varied every predetermined values only in the region with a bodily fluid by using the region division result at step S505 described above. In this case, when the lumen image is determined as that of a stomach at step S504, the image generating unit 10 excludes the color range of a bodily fluid including bile from those used for generating new images because bile is not present.

Thereafter, the learning unit 50 calculates a feature amount based on the new images generated by the image generating unit 10 and the original lumen image that is acquired through the image acquiring unit 2, and generates identification criteria by the publicly-known SVM or the like (step S507).

Subsequently, the identifying unit 60 identifies a subject based on the identification criteria that are generated by the learning unit 50 (step S508). After step S508, the image processing apparatus 1 ends this processing.

According to the fourth embodiment explained above, learning samples with colors that can appear in a lumen image can be generated and, therefore, appropriate learning results can be acquired.

Other Embodiments

The present disclosure can be implemented by executing an image processing program that is recorded in a recording device by a computer system such as a personal computer and a workstation. Moreover, this computer system can be connected to a device such as another computer system and a server through a local area network (LAN), a wide area network (WAN), or a public network such as the Internet, to be used. In this case, the image processing apparatus according to the first to the fourth embodiments can acquire image data of a lumen image through these networks, can output an image processing result to various kinds of output devices such as a viewer and a printer connected through these network, and can store an image processing result in a storage device connected to these networks, for example, in a recording medium that can be read by a reader connected to the network.

The present disclosure is not limited to the first to the fourth embodiments. Various embodiments can be formed by combining components disclosed in the respective embodiments and modifications. For example, some of the components out of the entire components described in the respective embodiments and modifications can be excluded, or components in other embodiments and modifications can be adopted and combined.

Furthermore, terms that has been described at least once with another broader or synonymous term in the specification or the drawings can be replaced with the other term at any part of the specification or the drawings. As described, various modifications and applications are possible within a range not departing from a gist of the disclosure.

As described, the present disclosure can include various embodiments not described herein, and various kinds of design changes or the like can be made within a range of a specific technical idea.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus comprising:
   a processor comprising hardware, wherein the processor is configured to:
   acquire a lumen image of a lumen of a living body;
   determine biometric information from the lumen image;
   determine range information on a range of at least one of a hue and a brightness based on the biometric information determined from the lumen image;
   generate a plurality of new images by changing at least one of a hue and a brightness of the lumen image to predetermined values based on the range information; and
   learn identification criteria to perform identification of a subject based on the plurality of new images.

2. The image processing apparatus according to claim 1, wherein the processor is configured to perform identification of the subject based on the identification criteria.

3. The image processing apparatus according to claim 1, wherein the processor is configured to:
   determine information of a bodily fluid in the lumen image as the biometric information; and
   determine the range information based on the information of the bodily fluid.

4. The image processing apparatus according to claim 3, wherein the processor is configured to acquire information relating to a color range of blood.

5. The image processing apparatus according to claim 4, wherein the processor is configured to determine a color range of red based on the information relating to a color range of blood.

6. The image processing apparatus according to claim 3, wherein the processor is configured to calculate information relating to a color range of bile.

7. The image processing apparatus according to claim 6, wherein the processor is configured to determine a color range of yellow based on the information relating to the color range of bile.

8. The image processing apparatus according to claim 3, wherein the processor is configured to calculate information relating to a color range according to presence or absence of the bodily fluid.

9. The image processing apparatus according to claim 8, wherein the processor is configured to determine a color range of red and a brightness based on the information relating to a color range according to presence or absence of the bodily fluid.

10. The image processing apparatus according to claim 3, wherein the processor is configured to calculate information relating to a color range of drug.

11. The image processing apparatus according to claim 3, wherein the processor is configured to determine:
    an organ type of the lumen image; and
    a type of the bodily fluid based on the organ type.

12. The image processing apparatus according to claim 1, wherein the processor is configured to:
    divide the lumen image into predetermined regions; and
    generate the plurality of new images in which at least one of a hue and a brightness is changed per region obtained by division.

13. The image processing apparatus according to claim 12, wherein the processor is configured to divide the lumen image into the predetermined regions based on information of a bodily fluid.

14. An image processing method that is performed by an image processing apparatus, the image processing method comprising:
    acquiring a lumen image of a lumen of a living body;
    determining biometric information from the lumen image;
    determining range information on a range of at least one of a hue and a brightness based on the biometric information determined from the lumen image;
    generating a plurality of new images by changing at least one of a hue and a brightness of the lumen image to predetermined values based on the range information; and
    learning identification criteria to perform identification of a subject based on the plurality of new images.

15. A non-transitory computer-readable recording medium on which an executable program is recorded, the executable program instructing a processor of an image processing apparatus to execute:
    acquiring a lumen image of a lumen of a living body;
    determining biometric information from the lumen image;
    determining range information on a range of at least one of a hue and a brightness based on the biometric information determined from the lumen image;
    generating a plurality of new images by changing at least one of a hue and a brightness of the lumen image to predetermined values based on the range information; and
    learning identification criteria to perform identification of a subject based on the plurality of new images.

16. The image processing apparatus according to claim 1, wherein the processor is configured to:
    access at least:
       a first predetermined range of at least one of a hue and a brightness associated with a first substance; and
       a second predetermined range of at least one of a hue and a brightness associated with a second substance; and
    determine the range information on the range of at least one of a hue and a brightness as including the first predetermined range and not including the second predetermined range based on the biometric information determined from the lumen image.

17. The image processing apparatus according to claim 16,
wherein the processor is configured to:
determine that the lumen imaged in the lumen image is part of a predetermined organ based on the biometric information determined from the lumen image; and
determine the range information on the range of at least one of a hue and a brightness as including the first predetermined range and not including the second predetermined range in response to determining that the lumen imaged in the lumen image is part of the predetermined organ.

18. The image processing apparatus according to claim 1, wherein the processor is configured to:
divide the lumen image into at least a first region and a second region based on the biometric information; and
generate the plurality of new images by changing at least one of the hue and the brightness of the first region of the lumen image and not the second region of the lumen image based on the range information.

\* \* \* \* \*